United States Patent [19]

Folkers et al.

[11] 4,374,828
[45] Feb. 22, 1983

[54] BIOLOGICALLY ACTIVE THYMONES FROM THE THYMUS

[75] Inventors: Karl Folkers; Teresa M. Kubiak; Henryk M. Stepien, all of Austin, Tex.; Naoki Sakura, Ohkuwa, Japan

[73] Assignee: Board of Reagents, The University of Texas System, Austin, Tex.

[21] Appl. No.: 199,997

[22] Filed: Nov. 17, 1980

[51] Int. Cl.$^3$ .............................................. A61K 37/00
[52] U.S. Cl. ................................ 424/177; 260/112 R; 424/95
[58] Field of Search .............. 424/95, 177; 260/112 R

[56] References Cited

U.S. PATENT DOCUMENTS 4,239,498 12/1980 Rule ....................................... 424/88
4,250,084 2/1981 Trainin .................................. 424/95

Primary Examiner—Sam Rosen
Attorney, Agent, or Firm—Arnold, White & Durkee

[57] ABSTRACT

A class of three substances has been isolated in highly purified form and in substantially pure form by utilizing thymus tissue as a source material. These three substances are designated thymone A, thymone B and thymone C. Thymones A and B are new peptides which yield approximately 13 and 14 individual amino acid moieties, respectively, on acid hydrolysis. Thymones A and B are chemically characterized by electrophoretic and chromatographic values which are appropriate for substances which are substantially pure. Thymone C was highly purified and its biological activity was reproducibly detected and measured. Thymones A, B and C stimulate the proliferation of lymphocytes. Thymone A stimulates the formation of cyclic adenosine monophosphate. Thymone B stimulates the formation of cyclic guanosine monophosphate.

The biological activities of these thymones to stimulate the proliferation of lymphocytes and the formations of cyclic nucleotides are basic hormonal functions for the therapeutic enhancement of the immune system in patients who have immune deficiencies from diverse causes.

4 Claims, No Drawings

BIOLOGICALLY ACTIVE THYMONES FROM THE THYMUS

BACKGROUND OF THE INVENTION

This invention relates to the isolation and purification of biologically active substances from thymus tissue.

A prerequisite for establishing that a mammalian organ has an endocrine function is a demonstration that cell-free extracts of the organ will replace specific biological functions of the organ. It is common knowledge that this criterion has been met for the thymus gland, because extracts from the thymus gland have been shown to restore deficiencies of immune function which are brought about by thymectomizing an animal, i.e., removal of the thymus gland. Consequently, it is believed that a hormone or hormones unique to the thymus gland control immune competence in man.

It is also common knowledge that there is a direct correlation between certain diseases of childhood, aging or senescence and thymus-dependent immunity. It is known that the thymus has already begun to atrophy when children are about 10 years in age, and that the decrease in size continues so that the size has decreased to a level of about 50% by 50 years, and that the size continues to diminish with advancing age. Common diseases related to aging include cancer, autoimmune diseases and infectious diseases.

Various investigators have proposed that a hormone or hormones of the thymus gland are peptides. Purified preparations, which are mixtures, have been obtained from thymus extracts, and peptides have been isolated which have diverse activities in biological assay systems which are relevant to the human immune system.

Miller, J. R. A. P. and Osoba, D., Ciba Found. Study Group 16, 62 (1963), provided direct evidence that the thymus produces a humoral factor which may be important to the control of immunity. The evidence was based upon the discovery that deficient immune responses in mice after neonatal thymectomy were prevented by the implantation of graphs of thymus tissue. In 1965, Osoba, D., J. Exp. Med. 122, 633 (1965), had the concept that thymus lymphocytes are functionally immature in situ, but when these lymphocytes leave the thymus, they are obtained immunological competence through maturation under the influence of a "competence-inducing factor" or hormone produced by the thymus. Osoba found that this "competence-inducing factor" was in the thymus and was not in the spleen or lymph nodes. These and studies by other investigators were largely physiological, and provided a basis for the entrance of new chemistry of fractionation towards the isolation of one or more such thymic hormones.

Abraham White was one of the Early investigators in the research to achieve purification by stepwise fractionation toward a factor or hormone. Allan Goldstein was one of his students in the research which started about 1965 and continued during subsequent years.

In 1975, Goldstein, A., standardized a purification through about five steps and designated the material as "fraction 5". They used this fraction 5 for diversified biological research and provided such fraction to other investigators and also for exploratory clinical studies in patients with immune deficiency diseases.

Fraction 5 has been important to study effectiveness of constituents in the thymus for the clinical treatment of thymus-dependent immunological diseases (Wara, D. W., Goldstein, A. L., Doyle, W. and Amman, A. J., New Engl. J. Med. 292, 70–74 (1975); Goldstein, A. L., Cohen, G. H., Rossio, J. K., Thurman, G. B., Brown, C. N. and Ulrich, J. T., Med. Clin. N. Amer. 60, 195–606 (1976)). Fraction 5 has also been reported to cause reversal of certain immunological parameters which are known to decrease in cancer patients (Goldstein, A. L., Cohen, G. H. and Thurman, G. B., Control of Neoplasia by Modulation of the Immune System, 241–253 (M. A. Chirigos, ed., Raven Press, NY) (1977)). When fraction 5 was used in a combined modality ot treat carcinoma of the lung by a randomized protocol, both survival time and number increased (Cohen, M. H., Chretien, P. B., Hide, D. C., Fossieck, B. E., Blum, P. A., Kenany, D. E., Lipson, S. D. and Minna, J. D., Proc. Amer. Assoc. for Cancer Res. 17, 117 (1978)).

Kook, A. I., Yakir, Y. and Trainin, N., Cell Immunol. 19, 151–157 (1975), described their purification and partial chemical characterization of their thymic humoral factor (THF). Preparations of their THF were used by Varsano et al. (Acta Paediatr. Scand. 66, 329 (1977)) to treat severe disseminated adenovirus infection, which was reported in 1977 to be successful. A preparation of THF was also used by Zaizov et al. (Biomedicine, 27, 105 (1977)) for therapy with immunosuppressed children who had lymphoproliferative neoplasia and generalized varicella.

These exemplary clinical studies with preparations from A. Goldstein et al. and Trainin et al. underscore the importance of the chemical isolation and elucidation of thymic factors and hormones.

A summary of purified preparations and isolated peptides from the thymus, particularly as they have been tested for cyclic nucleotide effects, has been made by Naylor and A. Goldstein (Life Sci. 25, 301–310 (1979)). Supplementing this summary of 1979, Low and A. Goldstein et al. announced in 1980 (Fourth Intl Congress of Immunology, Abstract No. 17.2.22.) that they have isolated two new thymic peptide, designated thymosin $\beta_3$ and $\beta_4$, which appear to act on stem cells. These two peptides have an MW of about 5000–5500.

In 1977, Goldstein, A., et al. (Proc. Nat'l. Acad. Sci. 24, 725–729) reported on the isolation and sequence of thymosin $\alpha_1$ from fraction 5, see also related U.S. Pat. No. 4,079,127.

Thymosin $\alpha_1$ is a peptide having 28 amino acids, and it has AcSer in the N-terminal position. The sequence is as follows.

AcSer-Asp-Ala-Ala-Val$^5$-Asp-Thr-Ser-Ser-Glu$^{10}$-Ile-Thr-Thr-Lys-Asp$^{15}$-Leu-Lys-Glu-Lys-Lys$^{20}$-Glu-Val-Val-Glu-Glu$^{25}$-Ala-Glu-Asn$^{28}$-OH

Synthetic thymosin $\alpha_1$ is an ongoing subject of diversified biological and clinical investigations.

Gideon Goldstein and his associates began their research upon the thymus about 1969, and have continued this research up to the present time.

In 1974, Goldstein, G., reported on the isolation of thymin from bovine tissue. Thymin was found to consist of two polypeptides which were designated thymin I and thymin II. These two peptides were found to induce marrow cells to develop as intrathymic lymphocytes.

In 1975, Schlesinger and Goldstein (Cell 5, 361–365) reported upon the sequence of thymopoietin II. Goldstein and his associates renamed their two polypeptides as thymopoietin I and II. The expressions thymin I and I were abandoned.

Thymopoietin II has the following sequence:

NH$_2$-Ser-Glu-Phe-Leu-Glu$^5$-Asp-Pro-Ser-Val-Leu$^{10}$-Thr-Lys-Glu-Lys-Leu$^{15}$-Lys-Ser-Glu-Leu-Val$^{20}$-Ala-Asn-Val-Thr$^{25}$-Leu-Pro-Ala-Gly-Glu$^{30}$-Gln-Arg-Lys-Asp-Val$^{35}$-Tyr-Val-Gln-Leu-Tyr$^{40}$-Leu-Gln-Thr-Leu-Thr$^{45}$-Ala-Val-Lys-Arg$^{49}$-COOH

Thymopoietin II differs from thymosin α$_1$ by having more amino acids, but the two peptides do have serine in a position 1 although Ser$^1$ in thymopoietin II is not acetylated. Both thymopoietin II and thymosin α$_1$ have free C-terminal carboxyl groups.

Thymopoietin II differs from thymopoietin II only as follows:

THYMOPOIETIN I: Gly$^1$Gln$^2$His$^{43}$

Weksler, M. E., Innes, J. B. And Goldstein, G. (J. Exp. Med. 148, 996 (1978)) reported in 1978 some immunological studies on aging by utilizing mice. They observed two immune responses which are related to the thymus and which are affected by aging. One response concerned the generation of IgG plaque-forming cells (PFC). The second response concerned the generation of PFC with high affinity for antigen. They found that thymectomy of the mice accelerated both of these two immune responses. They also found that a preparation of thymopoietin increased the immune function of the spleen cells of old mice.

Since thymopoietins I and II are peptides having a relatively large number of amino acids, forty-nine, they designed and synthesized smaller peptides on the basis that such small peptides might simulate the activities of the native peptide. On this basis, Goldstein, G., et al. (Science 204, 1309 (1979)) synthesized a pentapeptide which was found to have a biological activity that was characteristic of the thymic hormone, thymopoietin.

The synthetic pentapeptide has the sequence:
(H) Arg$^{32}$-Lys$^{33}$-Asp$^{34}$-Val$^{35}$-Tyr$^{36}$-OH This pentapeptide induced, in vitro, differentiation of murine prothymocytes to thymocytes. This pentapeptide also inhibited, in vitro, the differential induction of cells which had a B-lineage. These investigators concluded that these two activities of the pentapeptide are unique to thymopoietin.

Goldstein, G., et al. concluded that this synthetic pentapeptide may represent an active site of thymopoietin.

Nathan Trainin and his co-workers at the Weizmann Institute of Science in Israel initiated their study on a factor in the thymus about 1960, and Trainin and his successive associates have continued their studies to the present time. The basis of their study was the concept of the possible existence of a thymic humoral factor, which they designated THF, in due time.

In 1973, Trainin et al. reported upon the hormone-like activity of the THF which induced immune reactivity.

In 1974, Trainin et al. described data indicating that THF can induce immunocompetence through cAMp and DNA syntheses. During the period of 1975-6, Kook, A. I., Yakir, Y. and Trainin, N. (Adv. Exp. Med. Biol. 66, 215-220 (1976)) described chemical characterization data indicating that THF can be an acidic peptide having a molecular weight of ca. 3000 and which consists of ca. 31 amino acids.

Two amino acid compositions of preparations of THF were published in 1975 and 1976 as follows:

| 1975 | 1976 | |
|---|---|---|
| 4 | 3 | Asp |
| 1 | 2 | Thr |
| 5 | 3 | Ser |
| 8 | 5 | Glu |
| 2 | 1 | Pro |
| 5 | 3 | Gly |
| 2 | 2 | Ala |
| — | 1 | Val |
| 1 | 2 | Leu |
| — | 1 | Phe |
| 1 | 1 | Lys |
| 2 | 2 | Arg |
| — | 1 | Cys |
| 31 | 27 | |

In 1979, Rotter, V. and Trainin, N. (J. Immunol. 122, 414–420 (1979)) described a thymic plasma recirculating factor (TPRF). This factor was partially characterized as a peptide having a molecular weight of about 3000. Their biological data indicated that this factor may involved in T-cell maturation.

Alberto Astaldi, of the Central Laboratory of the Netherlands, appeared to have begun his investigations on the thymus about 1970. With his associates, Astaldi has published a series of interesting investigations up to the present time which are important, because the molecular weight of his apparent peptide appears to be lower than that of any other investigator in the field.

In 1978, Kruisbeek et al. (Cell. Immunol. 35, 145–147 (1978)) described a thymic epithelial culture supernatant (TES). They found that TES increased the antibody production to SRBC by spleen cells from athymic mice. Also, TES was found to induce a helper cell function in thymocytes.

In 1979, Wijermans et al. (Biochem. Biophys. Res. Commun. 86, 88–96 (1979)) described data showing the presence of a thymus-dependent factor in serum (SR). It was found by this group that SF increased cAMP levels and stimulated protein synthesis. Their data also indicated that SF is thymus-dependent.

In 1979, at the Miles International Symposium at Johns Hopkins University in July, Astaldi reported data on the chemical characterization of SF.

SF was apparently pure by the presence of "one spot" in TLC systems. It was estimated to have a molecular weight of less than 500 and probably to consist of four amino acids.

Jean Francois Bach and his associates appear to have initiated their investigations of the thymus about 1969, and have continued to make important contributions in this field up to the present time. During the early years, their investigations focused upon biological aspects of the thymus immunosuppression. Later, they undertook chemical purification studies on a factor.

In 1973, Bach et al. reported the demonstration of a circulating thymic hormone which they observed to be in the serum of normal mice, but not in the serum of athymic mice. This factor appeared to have a molecular weight of less than 10,000 on the basis of its passage through a membrane.

In 1977, Bach et al. described the isolation of a thymic peptide (FTS) from pig serum. They utilized a total of about 1000 liters of serum to achieve isolation of the peptide by steps including ultrafiltration, gel filtration and ion exchange chromatography.

FTS was found to be a nonapeptide which consisted of 1 Lys, 1 Asp(Asn), 2 Ser, 2 Glu(Gln), 2 Gly, 1 Ala.

Bach et al. (Nature 266, 55–57 (1977)) further characterized FTS in 1977, and described the sequence as:
<Glu-Ala-Lys-Ser-Gln-Gly-Gly-Ser-Asn-OH It can readily be appreciated from the foregoing description that the thymus organ is a source for various hormonal substances, not all of which have presently been identified. Consequently, there is much need for the purification, isolation and identification of the discrete components which are present in thymus extracts. Unless the components are purified to homogeneity, there is no suitable procedure available to elucidate the chemical structure and to ultimately synthesize these biologically valuable hormones for clinical studies.

SUMMARY OF THE INVENTION

This invention constitutes the recognition for the first time and by novel processes of a class of three substances which has been isolated in substantially pure form by utilizing thymus glands of calves as a source material. It is understood that other mammalian thymus glands are equally suitable tissues to obtain this class of substances by the novel processes, and that this initial use of tissue from calves was merely convenient.

The novel processes consist of multiple and sequential steps in one or more but related series. These processes results from extensive experimentation and the assembly of successful steps and the deletion of unsatisfactory steps.

Thymus tissue was reasonably freed of fatty tissue and lyophilized. The dehydrated tissue was defatted by methylene chloride. The defatted tissue was extracted with methanol, and the methanol extractives were next extracted with aqueous acetic acid. Combinations of gel filtration and ion exchange chromatography was used in sequences and in series and utilized Sephadex G-10, DEAE-Sephadex A-25, CM-Sephadex C-25, Bio-Gel P-6.

A fraction from Bio-Gel P-6 yielded substantially pure thymone A which was characterized by three electrophoretic values and by acid hydrolysis to give approximately 14 individual amino acids, and by its biological activities to stimulate the proliferation of lymphocytes and the formation of cyclic adenosine monophosphate (cAMP).

Thymone B was obtained substantially pure after a purification step utilizing Sephadex G-25, and was characterized by thin layer chromatographic and electrophoretic values, and by acid hydrolysis to give approximately thirteen amino acids, and by its biological activities to stimulate the proliferation of lymphocytes and the formation of cyclic guanosine monophosphate (cGMP).

Thymone C was obtained in a state of high purification from a fraction after CM-Sephadex C-25 chromatography and was found to stimulate the proliferation of lymphocytes.

The biological activities of significantly stimulating the proliferation of lymphocytes and the formation of cyclic nucleotides are basic hormonal functions for the therapeutic enhancement of the immune system in patients having immune deficiencies from diverse causes including bacterial and viral infections, therapy with immune suppressive drugs, cancer, etc.

DETAILED DESCRIPTION OF THE PREFERRED EMBODIMENTS

GENERAL METHODS AND MATERIALS

Chromatography was generally performed (particularly the large-scale operations) at 4° C. Lyophilization of the fractions was usually initiated within 1 hr after the fraction was eluted from the column. Sephadex gel was purchased from Sigma Chemical Co., St. Louis, MO. Precoated plates, Silica gel 60 (Merck and Co. Inc., Rahway, NJ) were used for TLC. Spots were visualized by spraying with ninhydrin solution (ninhydrin 0.3 g, n-BuOH 100 ml and AcOH 3 ml) followed by heating. Water used to prepare buffers for chromatography (and gel filtration) was deionized, distilled, and degassed prior to use.

DEHYDRATION OF THYMUS GLANDS

Thymus glands from calves (4–6 months in age) were received frozen within 15 hrs after the animals had been slaughtered. In order to facilitate the dehydration, the frozen glands were cut into pieces of approximately 5 cm$^3$. The frozen pieces of tissue were put into 1 and/or 2 l jars and lyophilized at 0.015–0.2 Torr for 5–7 days or until the tissue was dry and had reached room temperature. A Virtis Freezemobile II equipped with a 10-MR-24 manifold was used. If the dehydrated tissue could not be processed immediately, it was stored at −18° C. The lyophilization of the thymus tissue resulted in a weight reduction of 45–85% depending on the amount of fatty tissue associated with the thymus.

DEFATTING OF DEHYDRATED THYMUS TISSUE

A typical batch of 0.6 kg of dehydrated tissue was defatted by grinding at 4° C. for about 2 min. in 2 l of methylene chloride, pre-cooled to 4° C., using a Waring blender, Model CB-5, followed by filtering by water suction using a Büchner funnel and Whatman No. 1 filter paper (24 cm). This filtration and the following filtrations were performed at room temperature and each was completed within 15 min. The beige powder-like residue was, for practical reasons, divided into three equal parts; each part was placed in a Nalgene jar (one liter) and was separately treated. The volumes of solvents used for defatting and extraction are hereafter referred to on the basis of the total amount used for the three jars in each step. The residue was shaken with 1.5 l (0.5 l in each jar) methylene chloride (pre-cooled to 4° C.) for 30 min. at 4° C. and filtered, as described. To complete the defatting, the residue was shaken and filtered twice more, as described. The defatted residue was, if not processed immediately, stored under reduced pressure at −18° C.

EXTRACTION BY METHANOL OF THE DEFATTED THYMUS TISSUE

The defatted thymus residue was divided into three equal parts as described under the section Defatting of Dehydrated Thymus Tissue. Each part was extracted by shaking three times with 1.5 l of methanol (pre-cooled to 4° C.) for 30 min. at 4° C. with filtration, as described. The extracted tissue residue, which weighed approximately 0.37 kg after being dried at 0.05–0.4 Torr for 4 days, was stored at −18° C. for later extraction. The three methanol extracts were combined (total volume 4–4.5 l) and stored overnight at −18° C.

EVAPORATION OF METHANOL EXTRACT

The methanol was evaporated, in vacuo, using a Buchi Rotavapor and pump. Care was taken that the temperature of the extract did not exceed 15° C. The evaporation rate under these conditions was approximately 1 l/hr. The sticky, pale yellow-beige residue was suspended in distilled water to a volume of 564 ml. This volume corresponded to the capacity of the centrifugation rotor which was used. If the suspension was more concentrated, the sedimentation rate during centrifugation was unpractically slow. The suspension was stored in the frozen state, usually overnight, at −18° C.

CENTRIFUGATION AND LYOPHILIZATION OF METHANOL EXTRACTIVES

After thawing, the suspension was centrifuged at 80,000 x $g_{min}$ to 225,000 x $g_{max}$ for 4½ hrs at 3° C. using a Beckman L2-65 B or L8 centrifuge equipped with a 45 Ti rotor spun at 44,000 rpm. The semi-solid centrifugate was discarded, and the clear pale yellow supernatant (450 ml) was lyophilized to yield approximately 20 g of a pale yellow amorphous and hydroscopic residue.

EXTRACTION WITH ACETIC ACID AND DIALYSIS

A batch of the residue (300 g) from methanol extraction was extracted with 2 M AcOH (1500 ml) under vigorous shaking for 1 hr at 4° C. The mixture was centrifuged at 10,000 x g for 30 min at 4° C., using a Beckman J-21 centrifuge which was equipped with a JA-10 rotor at 10,000 rpm. The precipitate was discarded, and the supernatant was lyophilized to give 21.4 g of residue.

This residue was suspended in 1 M AcOH (260 ml) and ultracentrifuged at 44,000 rpm for 4.5 hr at 4° C. using a Beckman L8-80 ultracentrifuge which was equipped with a 45 Ti rotor.

The supernatant was introduced into dialysis sacs (Spectra/Por G, MW cut-off 8,000, flat width 32 mm) and dialyzed against 1 M AcOH (2 l) for 24 hrs with double changes of 1 M AcOH (2 l and 1 l) after 8 hrs and 16 hrs through the dialysis period. The diffusate (5 l) was lyophilized to yield 14.0 g of residue.

GEL FILTRATION OF ACETIC ACID EXTRACTIVES ON SEPHADEX G-10

The residue from the diffusate of dialysis was dissolved in 1 M AcOH (10 ml) and the small amount of insoluble material was removed by centrifugation at 3,000 rpm using IEC HN-S centrifuge (Damon/IEC Division). The supernatant was passed through a Sephadex G-10 column (5.2×97 cm) which had been equilibrated with 1 M AcOH. The eluate was collected in 10 ml fractions, which were pooled and lyophilized to give the following residues, as follows.

| Fractions | Weight |
| --- | --- |
| Fraction No. 71–80 | 53 mg |
| Fraction No. 81–92 | 191 mg |
| Fraction No. 93–107 | 1.02 g |
| Fraction No. 108–121 | 1.79 g |
| Fraction No. 122–135 | 2.80 g |

The data from the intrinsic proliferation lymphocyte (IPL) assay (see MATERIALS AND METHODS OF BIOASSAYS, infra, for detailed experimental explanation) of these fractions were as follows.

| Fractions | Level | cpm | P |
| --- | --- | --- | --- |
| Fraction No. 71–80 | 200 µg | 97 | <0.001 |
| Fraction No. 81–92 | 400 µg | 81 | <0.001 |
| Fraction No. 93–107 | 400 µg | 10,272 | n.s. |
| Fraction No. 108–121 | 400 µg | 11,379 | n.s. |
| Fraction No. 122–135 | 400 µg | 16,758 | n.s. |
| Control | — | 11,670 | — |

The void peak material from Sephadex G-10 (Fractions 71–80) was assayed several times, and the results were confirmatory. There was inhibitory activity. This inhibition activity of Fractions 71–80 was also evident on a dose(level)response basis, and it was not affected by concanalavin A (ConA) as revealed by the following two assays.

The IPL assay without ConA was as follows.

| Fractions | Level | cpm | P |
| --- | --- | --- | --- |
| Control | — | 4608 | — |
| Fraction No. 71–80 | 10 µg | 3556 | <0.05 |
| Fraction No. 81–92 | 20 µg | 3148 | <0.05 |
| Fraction No. 93–107 | 50 µg | 2574 | <0.01 |
| Fraction No. 108–121 | 100 µg | 131 | <0.001 |
| Fraction No. 122–135 | 200 µg | 80 | <0.001 |

The IPL assay was conducted with the use of ConA, and the results were as follows.

| Fractions | Level | cpm | P |
| --- | --- | --- | --- |
| Control | — | 60831 | — |
| Fraction No. 71–80 | 10 µg | 62627 | n.s. |
| Fraction No. 81–92 | 20 µg | 49628 | <0.05 |
| Fraction No. 93–107 | 50 µg | 28964 | <0.01 |
| Fraction No. 108–121 | 100 µg | 209 | <0.001 |
| Fraction No. 122–135 | 200 µg | 102 | <0.001 |

PURIFICATION OF POOLED FRACTIONS 71–80 BY DEAE-SEPHADEX A-25 CHROMATOGRAPHY

The pooled material from fractions 71–80 was purified on a column of DEAE-Sephadex A-25 (4.6×6 cm). The column was first washed with 200 ml of 0.01 M $NH_4HCO_3$, pH 8.25, followed by a linear gradient of 1 l of each 0.01 and 1 M $NH_4HCO_3$, pH 8.25. After lyophilization of twelve 10-ml fractions, the following weights of residues were obtained.

| Fractions | Weights |
| --- | --- |
| Fraction I | 105 mg |
| Fraction II | 35 mg |
| Fraction III | 20 mg |
| Fraction IV | 77 mg |
| Fraction V | 54 mg |
| Fraction VI | 24 mg |
| Fraction VII | 33 mg |
| Fraction VIII | 19 mg |
| Fraction IX | 4 mg |
| Fraction X | 3 mg |
| Fraction XI | 3 mg |
| Fraction XII | 5 mg |

The results of the assay by IPL of these twelve fractions are as follows. Fractions III to VI and VII-VIII and IX through XII were combined to give a total of 5 fractions. The conclusions of the assay are as follows.

| Fractions | |
|---|---|
| Fraction I | Inhibition of intrinsic proliferation of lymphocytes |
| Fraction II | No activity |
| Fractions III–VI | Activity of Thymone A |
| Fractions VII–VIII | No activity |
| Fractions IX–XII | Activity of Thymone B |

It was discovered that although pooled fractions 71–80 had strong inhibitory activity on IPL assay, the fractionation by DEAE-Sephadex A-25 not only primarily separated the inhibitory entity, but also revealed two stimulatory entities, thymone A and thymone B, which were not evident in fractions 71–80, because of the co-existence of the potent inhibitory factor(s).

PURIFICATION BY CM-SEPHADEX C-25 CHROMATOGRAPHY OF FRACTION 1 FROM DEAE-SEPHADEX A-25

Fraction I (100 mg) was dissolved in H$_2$O (50 ml, adjusted pH to 6.00) and the solution was passed over a column of CM-Sephadex C-25 (4.6×4 cm), which had been pre-equilibrated with 10 mM NH$_4$OAc (pH 6.00). This column was eluted subsequently with H$_2$O (50 ml), 10 mM NH$_4$OAc (200 ml; pH 6.00), a linear gradient of 400 ml each of 10 mM NH$_4$OAc and 0.5 M NH$_4$OAc (pH 6.00), a linear gradient of 200 ml each of 0.5 M NH$_4$OAc (pH 6.00) and 0.5 M NH$_4$OAc (pH 8.50), and finally with 2.8% NH$_4$OH (200 ml). The eluates were collected in 10-ml volumes and the elution profile was monitored at 254 nm.

Each fraction pooled (Fr. 1–8) was lyophilized, and the residue was relyophilized from H$_2$O and then completely desalted by Sephadex G-10 column (2.3×60 cm) using 1 M AcOH as eluent. The yields of residues were as follows.

| Source | Fraction | Weight |
|---|---|---|
| Eluates 1–30, | pooled as Fraction 1 | 7.0 mg |
| Eluates 31–50, | pooled as Fraction 2 | 0.7 mg |
| Eluates 51–60, | pooled as Fraction 3 | 4.1 mg |
| Eluates 61–75, | pooled as Fraction 4 | 13.0 mg |
| Eluates 76–97, | pooled as Fraction 5 | 15.7 mg |
| Eluates 98–114, | pooled as Fraction 6 | 12.5 mg |
| Eluates 115–133, | pooled as Fraction 7 | 12.5 mg |
| Eluates 134–152, | pooled as Fraction 8 | 3.5 mg |

The data from IPL assay of these fractions are as follows.

| | Fraction | Level | cpm | P |
|---|---|---|---|---|
| Eluates 1–30, | pooled as Fraction 1 | 50 µg | 11917 | n.s. |
| Eluates 31–50, | pooled as Fraction 2 | " | 12594 | n.s. |
| Eluates 51–60, | pooled as Fraction 3 | " | 14498 | n.s. |
| Eluates 61–75, | pooled as Fraction 4 | " | 10720 | n.s. |
| Eluates 76–97, | pooled as Fraction 5 | " | 14671 | <0.05 |
| Eluates 98–114, | pooled as Fraction 6 | " | 14714 | <0.05 |
| Eluates 115–133, | pooled as Fraction 7 | " | 12312 | n.s. |
| Eluates 134–152, | pooled as Fraction 8 | " | 418 | <0.001 |
| Control | | — | 11828 | — |

The inhibitory substance(s) was found in fraction 8, which was eluted from CM-Sephadex C-25 column with 2.8% NH$_4$OH after the elution with 0.5 M NH$_4$OAc buffer (pH 8.50). This result revealed a property of the inhibitory factor(s); It should be a very strong basic substance(s).

It was important that this ion-exchange chromatography separated thymone C in fractions 5 and 6 from the inhibitory substance(s) in fraction 8.

The retention time of thymone C on CM-Sephadex is similar to that of thymone A on the same chromatography (See following section on PURIFICATION ON CM-SEPHADEX C-25 OF FRACTIONS III THROUGH VI FROM DEAE-SEPHADEX TO GIVE THYMONE A).

These data indicate that both thymone A and thymone C may be slightly basic substances under these conditions of purification.

PURIFICATION OF FRACTION I FROM DEAE-SEPHADEX ON BIO-GEL P-6

Repetition twice of the preparation of fraction I from DEAE-Sephadex yielded 138 and 250 mg of residue, which were combined and dissolved in 1 M AcOH (2 ml). The solution was passed over a column of Bio-Gel P-6 (3.6×63 cm) which had been equilibrated with 1 M AcOH. The eluates were collected in 5-ml fractions, and were pooled as follows and lyophilized to yield the residues, as follows.

| Source | Fraction | Weight |
|---|---|---|
| Eluates 30–55, | pooled as Fraction 1 | 18.4 mg |
| Eluates 56–67, | pooled as Fraction 2 | 14.4 mg |
| Eluates 68–84, | pooled as Fraction 3 | 43.2 mg |
| Eluates 85–94, | pooled as Fraction 4 | 216.0 mg |
| Eluates 95–108, | pooled as Fraction 5 | 44.0 mg |
| Eluates 109–116, | pooled as Fraction 6 | 6.4 mg |
| Eluates 117–132, | pooled as Fraction 7 | 6.7 mg |

The data from the IPL assay of these seven fractions were as follows.

| | | Level | cpm | P |
|---|---|---|---|---|
| Eluates 30–55, | pooled as Fraction 1 | 50 µg | 4196 | n.s. |
| Eluates 56–67, | pooled as Fraction 2 | " | 4409 | n.s. |
| Eluates 68–84, | pooled as Fraction 3 | " | 652 | <0.001 |
| Eluates 85–94, | pooled as Fraction 4 | " | 103 | <0.001 |
| Eluates 95–108, | pooled as Fraction 5 | " | 76 | <0.001 |
| Eluates 109–116, | pooled as Fraction 6 | " | 6323 | n.s. |
| Eluates 117–132, | pooled as Fraction 7 | " | 7102 | n.s. |
| Control | | — | 5540 | — |

The inhibitory substance(s) was present in Fractions 3 through 6, but was largely in Fractions 4 and 5. This elution area correspond to MW>1000. Fractions 5 and 6 showed two main spots in several TLC systems.

This section on purification of Fraction I from DEAE-Sephadex primarily revealed the emergence of the inhibitory factor(s) which are different from thymones A, B and C.

PURIFICATION ON CM-SEPHADEX C-25 OF FRACTIONS III THROUGH VI FROM DEAE-SEPHADEX TO GIVE THYMONE A

The preparation of fractions III through VI was twice repeated to give a total of 150 mg of residue which was dissolved in H$_2$O (100 ml, adjusted pH to 6.00). The solution was passed over a column of CM-Sephadex C-25 (4.6×4 cm), which had been pre-equilibrated with 10 mM NH$_4$OAc (pH 6.00). This column was eluted subsequently with H$_2$O (100 ml), 10 mM NH$_4$OAc (100 ml; pH 6.00), a linear gradient of 400 ml each of 10 mM NH4OAc and 0.5 M NH4OAc (pH 6.00), a linear gradient of 200 ml each of 0.5 M NH4OAc (pH 6.00) and 0.5 M NH4OAc (pH 8.50) and then finally with 2.8% NH4OH (200 ml). The eluates were collected in 10 ml fractions, and were pooled as follows. Each fraction, through 7, was lyophilized, and the residue was relyophilized from H2O and then completely desalted by a Sephadex G-10 column (2.3×60 cm) using 1 M AcOH as eluent. The yields of residues from the fractions were as follows.

| Source | Fraction | Weight |
| --- | --- | --- |
| Eluates 3–33, | pooled as Fraction 1 | 35.3 mg |
| Eluates 34–61, | pooled as Fraction 2 | 4.0 mg |
| Eluates 62–75, | pooled as Fraction 3 | 27.0 mg |
| Eluates 76–90, | pooled as Fraction 4 | 21.5 mg |
| Eluates 91–123, | pooled as Fraction 5 | 10.5 mg |
| Eluates 124–144, | pooled as Fraction 6 | 3.7 mg |
| Eluates 145–161, | pooled as Fraction 7 | 0.2 mg |

The data from the IPL assay were as follows.

| Fraction | | Level | cpm | P |
| --- | --- | --- | --- | --- |
| Eluates 3–33, | pooled as Fraction 1 | 50μg | 13072 | n.s. |
| Eluates 34–61, | pooled as Fraction 2 | " | 12858 | n.s. |
| Eluates 62–75, | pooled as Fraction 3 | " | 11536 | n.s. |
| Eluates 76–90, | pooled as Fraction 4 | " | 10350(?) | n.s.(?) |
| Eluates 91–123, | pooled as Fraction 5 | " | 19850(?) | <0.001 |
| Eluates 124–144, | pooled as Fraction 6 | " | 10834 | n.s. |
| Eluates 145–161, | pooled as Fraction 7 | " | 10631 | n.s. |
| Control | | — | 11828 | n.s. |

The residue of Fraction 5 was reassayed, and resulted in the following conformation of stimulation activity.

| | Level | cpm | P |
| --- | --- | --- | --- |
| Fraction 5 | 50 μg | 16788 | <0.05 |
| Control | — | 5540 | |

Fraction 5 appeared to be a unique fraction to show stimulation in the IPL assay.

By ion-exchange chromatography with CM-Sephadex C-25 under the conditions described, thymone A was effectively concentrated in fraction 5.

GEL FILTRATION OF FRACTION 5 FROM CM-SEPHADEX ON BIO-GEL P-6

Fraction 5 from DEAE-Sephadex, 10 mg, was dissolved in 1 M AcOH (0.3 mg) and was passed over a column of Bio-Gel P-6 (1.03×105 cm) equilibrated with 1 M AcOH. The eluates were collected in 1.5-ml fractions, pooled as shown below and lyophilized (weights are shown).

| Source | Fraction | Weight |
| --- | --- | --- |
| Eluates 17–25, | pooled as Fraction 1 | 0.5 mg |
| Eluates 26–33, | pooled as Fraction 2 | 1.3 mg |
| Eluates 34–39, | pooled as Fraction 3 | 1.7 mg |
| Eluates 40–47, | pooled as Fraction 4 | 2.5 mg |
| Eluates 48–56, | pooled as Fraction 5 | 0.6 mg |
| Eluates 57–65 | pooled as Fraction 6 | 0.4 mg |

The results of the IPL assay on these six fractions were as follows.

| Fraction | | Level | | P |
| --- | --- | --- | --- | --- |
| Eluates 17–25, | pooled as Fraction 1 | 50 μg | 17854 | <0.01 |
| Eluates 26–33, | pooled as Fraction 2 | " | 14887 | n.s. |
| Eluates 34–39, | pooled as Fraction 3 | " | 15028 | <0.05 |
| Eluates 40–47, | pooled as Fraction 4 | " | 11258 | n.s. |
| Eluates 48–56, | pooled as Fraction 5 | " | 10522 | n.s. |
| Eluates 57–65, | pooled as Fraction 6 | " | 11808 | n.s. |
| Control | | — | 11828 | — |

The void peak of Bio-Gel P-6 had the activity of thymone A. This result indicated that thymone A has a MW≳6000.

GEL FILTRATION OF POOLED FRACTIONS III–VI FROM DEAE-SEPHADEX ON BIO-GEL P-6

The residue (9.1 mg) from the pooled fractions III–VI from DEAE-Sephadex was dissolved in 1 M AcOH (0.3 ml) and passed over a column of Bio-Gel P-6 (1.03×105 cm) equilibrated with 1 M AcOH. The eluate was collected in 1.5 ml fractions, and was pooled as follows and lyophilized.

| Source | Fraction | Weight |
| --- | --- | --- |
| Eluates 19–28, | pooled as Fraction 1 | 0.86 mg |
| Eluates 29–35, | pooled as Fraction 2 | 1.83 mg |
| Eluates 36–43, | pooled as Fraction 3 | 3.19 mg |
| Eluates 44–51, | pooled as Fraction 4 | 3.34 mg |
| Eluates 52–66, | pooled as Fraction 5 | 0.10 mg |

The results of the IPL assay in the five fractions were as follows.

| | Level | cpm | P |
| --- | --- | --- | --- |
| Fraction 1 | 30 μg/ml | 17561 | <0.01 |
| Fraction 2 | 50 μg/ml | 12610 | n.s. |
| Fraction 3 | 50 μg/ml | 15473 | n.s. |
| Fraction 4 | 50 μg/ml | 12707 | n.s. |
| Fraction 5 | 50 μg/ml | 9576 | n.s. |
| | 0 μg/ml | 11177 | — |

Fraction 1 from Bio-Gel P-6 revealed essentially one spot in electrophoresis in three solvent systems, each at a different pH, as follows.

1. 2000 V, 6 mA, 20 min., pyridine-acetic acid-water(1:10:190), pH 3.5
2. 800 V, 22 mA, 50 min., pyridine-acetic acid-water(4:1:45), pH 5.3
3. 2000 V, 6 mA, 15 min., pyridine-acetic acid-water(10:0.4:89.6), pH 6.45

Electrophoresis was performed on cellulose plates (10×20 cm) from E. Merck Darmstadt, Germany. The plates were sprayed with chlorine/o-tolidine reagent.

When lysine was used for reference in electrophoresis, the values were:

Rf=0.37; 800 V; 22 mA; 15 min; pH 5.3; System 2 above

Rf=0.33; 1000 V; 6 mA; 20 min; pH 3.5; System 1 above

Rf=0.28; 2000 V; 6 mA; 10 min; pH 6.45; System 3 above

| | Stimulation of Incorporation of [³H]-Thymidine into DNA | | |
| --- | --- | --- | --- |
| Substance | Level | cpm ± SEM | P |

| | | -continued | |
|---|---|---|---|
| Control | — | 6,942 ± 1355 | — |
| Thymone A | 5 μg | 17,223 ± 621 | <0.001 |
| | 1 μg | 15,634 ± 1069 | <0.001 |
| | 100 ng | 11,519 ± 468 | <0.02 |
| | 10 ng | 6,841 ± 1007 | n.s. |

| | Stimulation of cAMP by Thymone A | | |
|---|---|---|---|
| Substance | Level μg/ml | Incubation min. | cAMP pmoles/$10^7$ cells |
| Control | — | 0 | 3.57 ± 0.26 | — |
| Thymone A | 1 | 1 | 3.44 ± 0.53 | n.s. |
| " | | 5 | 4.36 ± 0.58 | P < 0.05 |
| " | | 10 | 7.14 ± 0.78 | P < 0.001 |
| " | | 20 | 7.04 ± 0.59 | P < 0.001 |
| " | | 30 | 5.57 ± 1.36 | P < 0.001 |

Fraction 1 was hydrolyzed in constant boiling hydrochloric acid in the presence of phenol for 24 hr at 110° C. The hydrolysate (corresponding to 20 μg) was analyzed for the amino acids.

| ESTIMATE OF AMINO ACID COMPOSTION | | | | |
|---|---|---|---|---|
| Analysis | | Molar Ratios | | No. |
| Amino Acid | $\times 10^{-2}$ μmoles | Based on Leu = 3 | Based on His = 2 | Amino Acid |
| 1. Asp | 1.00 | 4.10 | 4.46 | 4 (?5) |
| 2. Thr | 0.909 | 3.73 | 4.06 | 4 |
| 3. Ser | 1.355 | 5.56 | 6.05 | 6 |
| 4. Glu | 2.270 | 9.31 | 10.13 | 10 (?9) |
| 5. Pro | 1.876 | 7.69 | 8.38 | 8 |
| 6. Gly | 1.381 | 5.67 | 6.17 | 6 |
| 7. Ala | 1.305 | 5.35 | 5.83 | 6 (?5) |
| 8. Val | 0.765 | 3.13 | 3.42 | 3 (?4) |
| 9. Met | 0.181 | 0.741 | 0.80 | 1 |
| 10. Ile | 0.401 | 1.09 | 1.79 | 2 (?1) |
| 11. Leu | 0.731 | 3.0 | 3.26 | 3 |
| 12. His | 0.448 | 1.84 | 2.00 | 2 |
| 13. Lys | 2.722 | 11.17 | 12.15 | 12 (?11) |
| 14. Arg | 0.831 | 3.39 | 3.71 | 4 (?3) |
| | | | | ca. 71 (?68) |

The amino acids Cys, Tyr, Phe and Trp were apparently absent.

The numbers of 7 of the 14 amino acids were the same whether the numbers were based upon Leu=3 or His=2. The number of the other 7 amino acids varied by 1 for each amino acid depending upon whether the calculation was based upon Leu or His. On this basis, the total number of amino acids was estimated at 68-71 with an MW of ca. 7291-7677.

The behavior of the sample of thymone A over a standardized column (bovine serum albumin, luteinizing hormone-releasing hormone (LHRH), alanine) of Bio-Gel P-6 indicated that this peptide has a molecular weight of ≧6000.

An enzymatic degradation of 75 μg of thymone A was conducted with 0.1% trypsin by weight for 10 min. There was complete inactivation by the assay based upon the incorporation of tritiated thymidine into DNA, as follows.

| | Level | cpm |
|---|---|---|
| Control | — | 14344 |
| Thymone A | 75 μg | 15378 (n.s.) |

DESCRIPTION OF THE PREFERRED EMBODIMENTS OF THE ISOLATION OF THYMONE B

Thymone B was isolated from the methanol extractives by a combination of ion-exchange chromatography and gel filtration. The initial steps through the preparation of the methanol extractives were conducted from calf thymus glands as described for thymone A.

The methanol extractives were extracted with acetic acid by the same conditions which are described for the isolation of thymone A.

The acetic acid extractives were applied directly to a Sephadex G-50 column. The dialysis step was omitted.

PURIFICATION BY SEPHADEX G-50 OF THE ACETIC ACID EXTRACTIVES

A sample of 30 ml of the acetic acid extractives was applied to a Sephadex G-50 column (6×86 cm). Elution was with 1 M acetic acid. After collection of an initial eluate of 580 ml, fractions of 10 ml were collected and pooled and lyophilized to yield materials as follows.

| | | Assay | | | |
|---|---|---|---|---|---|
| | | weight (mg) | level | cpm | P |
| Eluates 1–25, | Fraction 1; | 0.1922 | 200 μg | 2472 | <0.01 |
| Eluates 26–45, | Fraction 2; | 0.0835 | " | 3175 | <0.01 |
| Eluates 46–65, | Fraction 3; | 0.0898 | " | 3263 | <0.01 |
| Eluates 66–85, | Fraction 4; | 0.0685 | " | 6909 | n.s. |
| Eluates 86–105, | Fraction 5; | 0.0485 | " | 50 | <0.001 |
| Eluates 106–125, | Fraction 6; | 0.2746 | " | 41 | <0.001 |
| Eluates 126–145, | Fraction 7; | 2.7181 | " | 8300 | n.s. |
| Eluates 146–165, | Fraction 8; | 0.1692 | " | 10142 | <0.01 |
| Eluates 166–185, | Fraction 9; | 0.0154 | " | 9818 | n.s. |
| Eluates 186–230, | Fraction 10; | 0.0018 | " | 8490 | n.s. |
| Control | | — | — | 7143 | |

Fractions 1–3 showed inhibition
Fraction 4 showed no activity
Fractions 5–6 showed inhibition
Fraction 7 showed no activity
Fraction 8 showed stimulation
Fractions 9–10 showed no activity

PURIFICATION BY DEAE-SEPHADEX A-25 CHROMATOGRAPHY OF FRACTION 8 FROM SEPHADEX G-50

Fraction 8 (169 mg) from Sephadex G-25 was dissolved in 100 ml of 0.01 M NH$_4$HCO$_3$, pH 8.25, and chromatographed on a DEAE-Sephadex A-25 column (2.5×50 cm). The column was first washed with 200 ml of starting buffer, followed by a linear gradient of 1 l of each 0.01 and 1 M NH$_4$HCO$_3$, pH 8.25. Eluates of 10 ml were collected and pooled as indicated.

Each of the pooled fractions was lyophilized and the residue was dissolved in a small volume of water. The solution was then frozen, and relyophilized. This procedure was repeated 3–5 times to remove NH$_4$HCO$_3$.

| | | Assay | | | |
|---|---|---|---|---|---|
| | | weight (mg) | level | cpm | P |
| Eluates 4–20, | Fraction 1; | 115.7 | 75 μg | 5983 | <0.01 |
| Eluates 21–30, | Fraction 2 | 6.4 | " | 2474 | <0.001 |
| Eluates 31–36, | Fraction 3 | 2.5 | " | 5882 | <0.01 |
| Eluates 37–45, | Fraction 4 | 2.0 | " | 8296 | n.s. |
| Eluates 46–54, | Fraction 5 | 5.8 | " | 8850 | n.s. |
| Eluates 55–64, | Fraction 6 | 26.5 | " | 10022 | n.s. |
| Eluates 65–68, | Fraction 7 | 6.4 | " | 9016 | n.s. |
| Eluates 69–78, | Fraction 8 | 31.6 | " | 9471 | n.s. |

|  | | Assay | | |
|---|---|---|---|---|
|  | | weight (mg) | level | cpm | P |
| Eluates 79–84, | Fraction 9 | 13.92 | " | 15189 | n.s. |
| Eluates 85–90, | Fraction 10 | 10.10 | " | 15411 | <0.001 |
| Eluates 91–98, | Fraction 11 | 7.5 | " | 23151 | <0.001 |
| Eluates 99–112, | Fraction 12 | 12.1 | " | 18992 | <0.001 |
| Control |  |  |  | 9306 | — |
| Control 113–120, | Fraction 13 | 4.5 | " | 16250 | <0.001 |
| Control 121–134, | Fraction 14 | 3.88 | " | 19452 | <0.001 |
| Control 135–155, | Fraction 15 | 3.11 | " | 23900 | <0.001 |
| Control 156–180, | Fraction 16 | 2.1 | " | 37784 | <0.001 |
| Control 181–210, | Fraction 17 | 2.48 | " | 35190 | <0.001 |
| Control 211–230, | Fraction 18 | 7.76 | " | 11610 | n.s. |
| Control | — | — | | 9306 | — |

Fractions 1–3 showed inhibition
Fractions 4–8 showed no activity
Fractions 9–17 showed stimulation
Fraction 18 showed no activity

PURIFICATION BY CM-SEPHADEX C-25 CHROMATOGRAPHY OF FRACTIONS 14–17 FROM DEAE-SEPHADEX

Fraction 14–17 from DEAE-Sephadex (11.5 mg) was dissolved in 30 ml of distilled water, and the pH was adjusted to 6.0 with NH$_4$OH. The solution was applied to a CM-Sephadex C-25 column (1.5×8 cm). The column was first washed with 30 ml of distilled water, followed by 50 ml of 0.01 M NH$_4$OAc, pH 6.0. Then, the linear gradient of 100 ml each of 0.01 M NH$_4$OAc (pH 6.0) and 0.5 M NH$_4$OAc (pH 6.0) was used, followed by a linear gradient of 100 ml each of 0.5 M NH$_4$OAc (pH 6.0) and 0.5 M NH$_4$OAc (pH 8.5). The final elution was made by 200 ml of 2.8% NH$_4$OH (pH 11.56), followed by 100 ml of 1 M NaCl. Fractions of about 5 ml were collected and pooled and lyophilized and desalted using Sephadex G-10 and 1 M AcOH (the void peak was collected).

The fractions and the results were as follows.

|  | | Assay | | |
|---|---|---|---|---|
|  | | weight | level | cpm | P |
| Eluates 1–10, | Fraction 1; | 10.9 mg | 25 µg | 19628 | n.s. |
| Eluates 11–15, | Fraction 2; | 0.208 mg | " | 16190 | n.s. |
| Eluates 16–20, | Fraction 3; | 0.075 mg | " | 16808 | n.s. |
| Eluates 21–40, | Fraction 4; | 0.976 mg | " | 11595 | <0.001 |
| Eluates 41–55, | Fraction 5; | 0.320 mg | " | 13245 | <0.001 |
| Eluates 56–78, | Fraction 6; | 0.348 mg | " | 11103 | <0.001 |
| Eluates 79–90, | Fraction 7; | 0.050 mg | 5 µg | 12517 | n.s. |
| Eluates 91–100, | Fraction 8; | 0.422 mg | 25 µg | 36625 | <0.001 |
| Control |  | — | — | 15782 | — |
| Control 101–110, | Fraction 9; | 0.386 mg | 25 µg | 34934 | <0.001 |
| Control 111–123, | Fraction 10; | 0.422 mg | " | 36316 | <0.001 |
| Control 124–130, | Fraction 11; | 0.415 mg | " | 26262 | <0.001 |
| Control (100 ml washings) | 12; | 1.59 mg | " | 15720 | n.s. |
| Control |  | — | — | 15782 | — |

Fraction 1 showed little or no stimulation (thymone C)
Fractions 2–3 showed no activity
Fractions 4–6 showed inhibition
Fraction 7 showed little or no stimulation
Fraction 8–11 showed stimulation
Fraction 12 showed no activity

PURIFICATION BY CM-SEPHADEX C-25 CHROMATOGRAPHY OF FRACTIONS 9–13 FROM DEAE-SEPHADEX

Fraction 9–13 from DEAE-Sephadex (46.1 mg) was dissolved in 30 ml of distilled water (pH was adjusted to 6.0 with NH$_4$OH and applied to a CM-Sephadex C-25 column, 1.5×8 cm). The column was washed with 30 ml of distilled water, followed 50 ml of 0.01 M NH$_4$OAc (pH 6.0). Then, the linear gradient of 100 ml each of 0.01 M NH$_4$OAc (pH 6.0) and 0.5 M NH$_4$OAc (pH 6.0) was used, followed by a linear gradient of 100 ml each of 0.5 M NH$_4$OAc and 0.5 M NH$_4$OAc (pH 8.5). Final elution was made by 160 ml of 1% NH$_4$OH (pH 11.25) and 100 ml of 2.8% NH$_4$OH (pH 11.6) and 100 ml of 1 M NaCl. Fractions of 5 ml were collected and pooled, lyophilized, and desalted using a Sephadex G-10 column (void peak, 1 M AcOH).

|  |  | | Assay | | |
|---|---|---|---|---|---|---|
|  |  | | weight (mg) | level | cpm | P |
| Eluates | 1–13, | Fraction | 1; | 40 | 25 µg | 17769 | <0.01 |
|  | 14–33, | | 2; | 0.4 | " | 9675 | n.s. |
|  | 34–40, | | 3; | 0.8 | " | 7030 | n.s. |
|  | 41–49, | | 4; | 0.22 | " | 9567 | n.s. |
|  | 50–62, | | 5; | 0.87 | " | 7503 | n.s. |
|  | 63–72, | | 6; | 0.47 | " | 9130 | n.s. |
|  | 73–88, | | 7; | 0.39 | " | 9612 | n.s. |
|  | 89–98, | | 8; | 0.49 | " | 103 | <0.001 |
|  | 99–106, | | 9; | 0.46 | " | 147 | <0.001 |
| Control |  |  |  | — | — | 8075 | — |
|  | 107–118, | | 10; | 1.15 | " | 13895 | <0.001 |
|  | 119–124, | | 11; | 0.43 | " | 9216 | n.s. |
|  | 125–132, | | 12; | 0.54 | " | 22697 | <0.001 |
|  | 133–142 | | 13; | 1.34 | " | 14688 | <0.001 |
| (washings with 100 ml 1 M NaCl) |  |  | 14; |  | " | 7670 | n.s. |

-continued

| | Assay | | |
|---|---|---|---|
| | weight (mg) | level | cpm | P |
| Control | — | | 8075 | — |

Fraction 1 showed stimulation (thymone C)
Fractions 2–7 showed no activity
Fractions 8–9 showed inhibition
Fractions 10–13 showed stimulation

PURIFICATION BY SEPHADEX G-25 CHROMATOGRAPHY OF FRACTION 13 FROM CM-SEPHADEX C-25

Fraction 13 from CM-Sephadex C-25 (1.34 mg) was dissolved in 1 ml of 1 M acetic acid and applied to a Sephadex G-25 column (1×20 cm). The column was washed with 1 M acetic acid. The fractions of 0.5 ml were collected, pooled and lyophilized to yield the residues, as follows.

| | | | Assay | | | |
|---|---|---|---|---|---|---|
| | | | weight $\times 10^{-1}$ mg | level | cpm | P |
| Eluates | 1–10, | Fraction 1; | 0.36 | 100 ng | 9513 | n.s. |
| | 11–25, | 2; | 0.46 | " | 9012 | n.s. |
| | 26–34, | 3; | 0.38 | " | 9370 | n.s. |
| | 35–46, | 4; | 0.54 | " | 10532 | n.s. |
| | 47–56, | 5; | 0.37 | " | 9815 | n.s. |
| | 57–64, | 6; | 0.30 | " | 10628 | n.s. |
| | 65–74, | 7; | 0.47 | " | 12886 | <0.05 |
| | 75–84, | 8; | 0.38 | " | 11444 | n.s. |
| | 85–93, | 9; | 0.38 | " | 10395 | n.s. |
| | 94–110, | 10; | 0.70 | " | 10390 | n.s. |
| | 111–120, | 11; | 0.67 | " | 10906 | n.s. |
| | 121–135 | 12; | 0.97 | " | 10570 | n.s. |
| | 136–150, | 13; | 1.18 | " | 10305 | n.s. |
| | 151–178, | 14; | 0.5 | " | 10290 | n.s. |
| Control | | | — | — | 9780 | — |

Only Fraction 7 of the 14 fractions was active ($P < 0.05$) at a level of 100 nanograms.

ASSAYS WITH FRACTION 7 FROM SEPHADEX G-25

Examination of fraction 7 for purity by electrophoresis afforded the following data: Rf=0.05, relative to Lys; pyridine:AcOH:$H_2O$(2.6:30:867) pH 3.5; 1000 V, 3 mA, 20 min: cellulose plate(Merck) 5×20 cm. Examination for purity by TLC (Silica gel plates, 5×10 cm) gave the following results:

Rf=0.53; n-BuOH:Pyridine:AcOH:$H_2O$ (30:30:6:24)
Rf=0.48; EtOAc:Pyridine:AcOH:$H_2O$ (5:5:1:3)
Rf=0.61; n-BuOH:AcOH:EtOAc:$H_2O$ (1:1:3:1)

After hydrolysis of 20 μg of fraction 7 with hydrochloric acid under the usual conditions, the analysis for amino acids resulted in the data in Table I. Cys, Met, Tyr, Phe, and Trp were apparently absent.

TABLE I

| Amino Acid Analysis of Thymone B | | | |
|---|---|---|---|
| Amino Acid | $\times 10^{-2}$ μmoles | Amino Acid | $\times 10^{-2}$ μmoles |
| Asp | 0.369 | Ala | 0.432 |
| Thr | 0.237 | Val | 0.189 |
| Ser | 1.017 | Ile | 0.084 |
| Glu | 0.783 | Leu | 0.118 |
| Pro | 0.214 | His | 0.635 |
| Gly | 1.005 | Lys | 0.160 |
| | | Arg | 0.229 |

An advanced fraction after DEAE-Sephadex A-25 of thymone B (ca. 1 mg) was dissolved in 1 ml of 0.1 M N-ethyl-morpholine acetate buffer, pH 8.2. Digestion was carried out both with 0.2% and 1% of trypsin. The action of trypsin was terminated by addition of a trypsin inhibitor (1:1, w/w).

After 10 and 100 min, at a concentration of 0.2% trypsin, the activity in the assay for the incorporation of [$^3$H]-thymidine was 34,143 cpm ($p<0.02$) and 33,236 cpm ($p<0.05$), respectively, in comparison with the control value of 35,045 cpm before treatment. However, after digestion for 7 hrs, the level of cpm had decreased to 24,237 ($p<0.001$). At a concentration of 1% trypsin, the activity had decreased from an initial value of 35,045 cpm ($p<0.001$) to 30,535 cpm ($p<0.001$) and 21,605 cpm ($p<0.001$ after 10 and 100 min, respectively, and had decreased to 18,946 cpm ($p<0.001$) after 7 h.

Biological Assays

Incorporation of [$^3$H]-Thymidine into DNA

Fraction 7 from Sephadex G-25 was shown to have activity to stimulate the incorporation of [$^3$H]-thymidine into DNA, according to the data in Table II.

TABLE II

| Stimulation of Incorporation of [$^3$H]-Thymidine into DNA | | | |
|---|---|---|---|
| Substance | Level | cpm ± SEM | |
| Control | — | 13,513 ± 1394 | — |
| Fraction 7 of Thymone B | 30 μg | 39,388 ± 1278 | <0.001 |
| | 1 μg | 19,081 ± 271 | <0.02 |
| | 0.1 μg | 15,323 ± 489 | n.s. |
| Control | — | 9,780 ± 1028 | — |
| Fraction 7 of Thymone B* | 0.1 μg | 12,886 ± 320 | <0.05 |

*from Sephadex G-25

Stimulation of Synthesis of cGMP by Fraction 7 from Sephadex G-25

The same fraction from DEAE-Sephadex which was used to obtain the data in Table II was used in tests for possible stimulation of levels of cyclic nucleotides. The data in Table III show that this fraction of thymone B stimulates the synthesis of cGMP. These data in Table III show the stimulation with time as a variable. The data in Table IV show the stimulation of the level of the fraction of thymone B as a variable.

TABLE III

Stimulation of cGMP Synthesis

| Substance | Level µg/ml | Time min. | cGMP fmols/$10^6$ cells ± SEM | P |
|---|---|---|---|---|
| Control | 0 | 0 | 6.95 ± 0.89 | — |
| Fraction 7 of Thymone B | 100 | 1 | 7.77 ± 0.96 | n.s. |
| " | " | 5 | 10.66 ± 1.33 | <0.001 |
| " | " | 10 | 11.45 ± 1.12 | <0.001 |
| " | " | 20 | 6.01 ± 2.82 | n.s. |

TABLE IV

Stimulation of cGMP Synthesis

| Substance | Level µg/ml | Time min. | cGMP fmols/$10^6$ cells + SEM | P |
|---|---|---|---|---|
| Control | 0 | 0 | 6.60 ± 0.84 | — |
| Fraction 7 of Thymone B | 100 | 10 | 11.40 ± 0.87 | <0.001 |
| | 10 | " | 9.29 ± 1.15 | <0.001 |
| | 1 | " | 7.51 ± 2.12 | n.s. |

The same fraction 7 of thymone B was also tested for the stimulation of the synthesis of cAMP when the time of incubation and the level of thymone B were variables. After periods of 1, 5, 10, 20 and 30 min, a level of 100 µg/ml did not result in any statistically significant increase or decrease; the control value was 3.39 pmoles of cAMP/$10^7$ cells. At levels of 0.01, 0.1 1, 10 and 100 µg during an incubation of 10 min, there was no significant increase or decrease in the levels of cAMP in comparison with the control value of 3.75 pmoles of cAMP/$10^7$ cells.

MATERIALS AND METHODS OF BIOASSAYS

Male intact or neonatally thymectomized C57BL/6 mice, which were 6–8 weeks old, were obtained from the Charles River Breeding Labs., Inc., Wilmington, MA.

The Assay Based upon the Intrinsic Proliferation of Lymphocytes (IPL)

The prime measurement of this assay is the incorporation of [$^3$H]-thymidine into DNA.

Preparation of Cultures of Spleen Cells

The spleens of the mice were asceptically removed and immediately transferred to the RPMI-1640 medium (Gibco, Grand Island, NY) which had been buffered with 10 mM Hepes (Calbiochem, La Jolla, CA). The spleens were washed twice with ca. 5 ml each of the same medium. Blood clots were carefully removed and the suspension of spleen cells was obtained by enzymatic digestion with 0.1% of collagenase (Millipore Corp., NY). After a 15-min period of exposure to collagenase, the cells were centrifuged at 250×g for 7 min and were then resuspended in Tris-buffer containing 0.87% of ammonium chloride to lyse the erythrocytes (Boyle, W., *Transplantation* (1968) 6, 761–764). After a 10-min period of incubation at 37° C. in this buffer, the cells were then washed with 5 ml, three times, with the RPMI-1640 medium, which had been buffered with Hepes to pH 7.4 and supplemented with penicillin (100 U/ml) and streptomycin (100 µg/ml). After washing, the cells were resuspended in 10 ml of the same medium with 10% heat inactivated fetal calf serum (KC Biological Inc., Lenexa, KS), and the mixture was incubated at 37° C. in an atmosphere of $O_2$ and $CO_2$ (95:5 v/v) to allow the cells to stabilize. This procedure yielded a population containing >95% of viable cells as estimated by staining with a solution of 0.05% trypan blue.

Exposure of Cells to Fractions for Assay

After the 30-min period of incubation for stabilization, the cells were counted and then resuspended in fresh RPMI-1640 medium, containing 10% fetal calf serum (KC Biological Inc., Lenexa, KS), to a concentration of $1 \times 10^6$ cells/ml. Then, the cells were subdivided by introducing 1 ml suspension into plastic tubes (12×75 mm), supplied by Kimble Products (Houston, TX) in triplicate. The fractions to be tested had been dissolved in 100 µl of the RPMI-1640 medium at the desired concentrations, and then this solution was added to the suspension of the cell cultures, and the mixture, exposed to an atmosphere of oxygen and 5% $CO_2$, was incubated for 52 hrs at 37° C.

Incorporation of [$^3$H]-Thymidine

After the incubation of the cells and the fraction for 52 hr, 2 µCi of [$^3$H]-thymidine, having a specific activity of 20 Ci/mmol (New England Nuclear, Boston, MA) was added in 50 µl of RPMI-1640 medium. Twenty hours later, the cells were washed twice with 2 ml each time of the cold solution of 0.9% NaCl. The DNA was precipitated by adding 6 ml of cold aqueous 5% trichloroacetic acid. The precipitate was collected on Whatman Glass Microfibre filters GF/A, size 5-5 cm (Whatman, Ltd., England). The material on the filters was washed with 3 ml of absolute ethanol, and after drying at room temperature for 30 min, the material was introduced into the vials for counting with 10 ml of the scintillation liquid. The determination of cpm/min was conducted with a Beckman Liquid Scintillation Counter.

Determinations of cAMP and cGMP

The spleenic lymphocytes, $1.5 \times 10^7$, were exposed to the fractions to be assayed which had been dissolved in 100 µl of the RPMI-1640 medium at 37° C. in a water bath. The biological reaction was stopped by immersion of the incubate into a dry ice-ethanol bath to inactive phosphodiesterase for 1 min. Both assays were performed on fractions that had been lyophilized and resuspended in 0.5 ml of 0.05 M of sodium acetate buffer, pH 6.2, before addition of aliquots to the medium for assay.

The steps of purification and extraction of the cyclic nucleotides were performed according to the method of Yamamoto, I. and Webb, D. (Proc. Nat'l. Acad. Sci. USA 72, 2320–2324 (1975)). After the inactivation of phosphodiesterase, the suspension of cells was placed in a boiling water bath for 4 min. The extraction of the cyclic nucleotides from the samples was performed using 0.2 ml of a Dowex (formate from Dowex AG, 1-X8, 200–400 mesh, Sigma Chemical Co., St. Louis, MO)-water slurry(1:1). The Dowex suspension was vortexed 3 times over a 15-min period and then centrifuged at 2500 rpm for 10 min. The supernatant was discarded. The pellet was washed three times during 10 min with 0.8 ml of 4 N redistilled formic acid each time. This procedure released both cAMP and cGMP from the Dowex. The formic acid extract was then lyophilized and stored at −20° C. until the time of the RIA. The recovery of cAMP and cGMP was estimated by [³H]-radiolabeled cyclic nucleotide to be >85%.

The determination of the levels of cAMP and cGMP were performed by using the kits from the New England Nuclear, Boston, MA, according to the radioimmunological procedure of Steiner et al. (J. Biol. Chem. 247, 1106–1113 (1972)). In order to increase the sensitivity of the assay for cGMP, the samples were initially acetylated with a mixture of 5 μl of acetic anhydride and triethylamine (1:2 v/v) according to Harper and Brooker (J. Cyclic Nucl. Res. 1, 207–218(1975)).

The specificity and cross-reactivity of the cAMP and cGMP antiserum with several nucleotides with and without the acetylation step were found to be similar to that reported in the specifications for determination of cAMP and cGMP by the New England Nuclear.

All of the assays were performed in triplicate and the data were calculated as mean values±SEM. The student's t-test was used to determine statistical significance.

The Bioassay of cAMP and cGMP

The determinations of cAMP and cGMP utilized kits provided by the New England Nuclear, Boston, MA. The procedures of radioimmunoassay were based upon reports, as follows.

Steiner et al. (J. Biol. Chem. 247, 1106 (1972)), reported on a radioimmunoassay for cyclic nucleotides. Frandsen et al. (Life Sci. 18, 529 (1976)), described a simple ultrasensitive method to assay cAMP and cGMP in tissues. Naylor et al. (Immunopharmacology 1, 89 (1979)), examined the changes in cyclic nucleotides in murine lymphocytes after exposure to fraction 5 (thymosin).

The details of these assay methods will be published separately, and particularly after refinement of the assay based upon the stimulation of the incorporation of [³H]-thymidine by spleen cells.

SIGNIFICANCE OF THYMONES A, B AND C

A comparison of the chemical characteristics and the amino acid compositions and the biological activities of thymones A and B with known properties of all previously described peptides by other investigators, particularly, the thymosins, and the thymopoietins and the facteur thymique serique and the serum factor show that thymones A and B are different from these previously described peptides. Consequently, thymones A and B are new products. When thymone C is obtained in a state of substantial purity, its properties can be compared with those of all previously known substances for identity or newness.

The usefulness of thymones A, B and C is revealed by their basic biological activities which are characteristic of hormonal functions, particularly the stimulation of the proliferation of lymphocytes and the stimulation of the formation of cyclic nucleotides.

The usefulness of these thymones is for the therapeutic enhancement of depressed or a deficiency of immunocompetence in man. The usefulness is realized by the practical clinical administration of these thymones to patients who have such depressed immunocompetence that diseases occur, including autoimmune diseases, cancer and the complex deterioration of life known as aging.

Although the invention has been described in terms of particular preferred embodiments and examples, it will be apparent to those skilled in the art that various changes may be made in the processes described without departing from the scope of the invention.

We claim:

1. A class of biologically active substances from thymus tissue consisting essentially of thymone A, having
   an electrophoretic Rf of 0.37, relative to lysine, in the solvent system, pyridine-acetic acid-water (4:1:45) at pH 5.3, 800 V, 22 mA, 15 min. (cellulose plates, 10×20 cm);
   an electrophoretic Rf of 0.33, relative to lysine, in the solvent system, pyridine-acetic acid-water (1:10:190) at pH 3.5, 1000 V, 6 mA, 20 min. (cellulose plates, 10×20 cm);
   an electrophoretic Rf of 0.28, relative to lysine, in the solvent system pyridine-acetic acid-water (10:0.4:89.6) at pH 6.45, 2000 V, 6 mA, 10 min. (cellulose plates, 10×20 cm);
   approximately 68 to 71 amino acid; as moieties representing approximately 14 amino acids: aspartic acid—4 to 5 units; threonine—4 units; serine—6 units; glutamic acid—9–10 units; proline—8 units; glycine—6 units; alanine—5 to 6 units; valine—3 to 4 units; methionine—1 unit; isoleucine—1 to 2 units; leucine—3 units; histidine—2 units; lysine—11 to 12 units; arginine—3 to 4 units; and
   biological activities to stimulate the proliferation of lymphocytes and the formation of cyclic adenosine monophosphate;
thymone B, having
   an electrophoretic Rf of 0.05, relative to lysine; phridine:AcOH:H$_2$O (2.6:30:876) pH 3.5; 1000 V, 3 mA, 20 min. (cellulose plates 5×20 cm);
   a TLC Rf of 0.53; n-BuOH:pyridine:AcOH:H$_2$O (30:30:6:24) (Silica gel plates, 5×10 cm);
   a TLC Rf of 0.48; EtOAc:pyridine:AcOH:H$_2$O (5:5:1:3) (Silica gel plates, 5×10 cm);
   a TLC Rf of 0.61; n-BuOH:AcOH:H$_2$O (1:1:3:1) (Silica gel plates, 5×10 cm);
   as moieties representing approximately the 13 amino acids: aspartic acid, threonine, serine, glutamic acid, proline, glycine, alanine, valine, isoleucine, leucine, histidine, lysine, arginine; and
   biological activities to stimulate the proliferation of lymphocytes and the formation of cyclic guanosine monophosphate; and
thymone C, having the ability to stimulate the proliferation of lymphocytes,
   being extractable by methanol or acetic acid from defatted thymus tissue,
   having a retention time similar to thymone A on CM-Sephadex chromatography, and
   being separated from lymphocyte proliferation inhibitory substances by chromatography on DEAE-Sephadex A-25 chromatography followed by CM-Sephadex C-25 chromatography.

2. A biologically active substance extracted from thymus tissue consisting essentially of thymone A, having
   an electrophoretic Rf of 0.37, relative to lysine, in the solvent system, pyridine-acetic acid-water (4:1:45) at pH 5.3, 800 V, 22 mA, 15 min. (cellulose plates, 10×20 cm);
   an electrophoretic Rf of 0.33, relative to lysine, in the solvent system, pyridine-acetic acid-water (1:10:190) at pH 3.5, 1000 V, 6 mA, 20 min. (cellulose plates, 10×20 cm);

an electrophoretic Rf of 0.28, relative to lysine, in the solvent system, pyridine-acetic acid-water (10:0.4:89.6) at pH 6.45, 2000 V, 6 mA, 10 min. (cellulose plates, 10×20 cm);

approximately 68 to 71 amino acids, as moieties representing approximately 14 amino acids: aspartic acid—4 to 5 units; threonine—4 units; serine—6 units; glutamic acid—9–10 units; proline—8 units; glycine—6 units; alanine—5 to 6 units; valine—3 to 4 units; methionine—1 unit; isoleucine—1 to 2 units; leucine—3 units; histidine—2 units; lysine—11 to 12 units; arginine—3 to 4 units; and biological activities to stimulate the proliferation of lymphocytes and the formation of cyclic adenosine monophosphate.

3. A biologically active substance extracted from thymus tissue consisting essentially of thymone B, having an electrophoretic Rf of 0.05, relative to lysine; pyridine:AcOH:H$_2$O (2.6:30:876) pH 3.5; 1000 V, 3 mA, 20 min. (cellulose plates 5×20 cm), a TLC Rf of 0.53; n-BuOH:pyridine:AcOH:H$_2$O (30:30:6:24) (Silica gel plates, 5×10 cm);

a TLC Rf of 0.48; EtOAc:pyridine:AcOH:H$_2$O (5:5:1:3) (Silica gel plates, 5×10 cm);

a TLC Rf of 0.61; n-BuOH:AcOH:EtOAc:H$_2$O (1:1:3:1) (Silica gel plates, 5×10 cm);

as moieties representing approximately the 13 amino acids: aspartic acid, threonine, serine, glutamic acid, proline, glycine, alanine, valine, isoleucine, leucine, histidine, lysine, arginine; and biological activities to stimulate the proliferation of lymphocytes and the formation of cyclic guanosine monophosphate.

4. A biologically active substance extracted from thymus tissue consisting essentially of thymone C, having the ability to stimulate the proliferation of lymphocytes, being extractable by methanol or acetic acid from defatted thymus tissue, having a retention time similar to thymone A on CM-Sephadex chromatography, and being separated from lymphocyte proliferation inhibitory substances by chromatography on DEAE-Sephadex A-25 chromatography followed by CM-Sephadex C-25 chromatography.

* * * * *